United States Patent [19]
Peng et al.

[11] Patent Number: 5,861,138
[45] Date of Patent: *Jan. 19, 1999

[54] LIGANDS FOR MRI CONTRAST AGENT

[75] Inventors: Wei-Jun Peng; Daniel A. Aguilar, both of Corpus Christi, Tex.

[73] Assignee: Hoechst Celanese Corp., Somerville, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 752,763

[22] Filed: Nov. 20, 1996

[51] Int. Cl.$^6$ ............................ A61K 51/00; A61M 36/14
[52] U.S. Cl. ............................ 424/1.65; 534/550; 540/1; 544/1; 544/3; 546/1; 548/400; 549/1; 549/4; 549/200
[58] Field of Search .......................... 546/2, 5, 6, 261, 546/263, 264, 265, 266, 1, 152, 184; 534/15, 16, 550, 558; 424/1.11, 1.65; 540/1; 544/1, 3; 548/400; 549/1, 4, 200

[56] References Cited

U.S. PATENT DOCUMENTS

| | | | |
|---|---|---|---|
| 4,001,323 | 1/1977 | Felder et al. | 260/559 |
| 4,153,795 | 5/1979 | Matsuda | 546/2 |
| 4,250,113 | 2/1981 | Nordal et al. | 564/153 |
| 4,396,598 | 8/1983 | Lin | 424/5 |
| 4,647,447 | 3/1987 | Gries et al. | 424/9 |
| 4,687,659 | 8/1987 | Quay | 424/9 |
| 4,719,098 | 1/1988 | Weinmann et al. | 424/9 |
| 4,837,169 | 6/1989 | Toner | 436/546 |
| 4,885,363 | 12/1989 | Tweedle et al. | 540/465 |
| 4,916,246 | 4/1990 | Felder et al. | 556/1 |
| 4,957,939 | 9/1990 | Gries et al. | 514/492 |
| 4,960,895 | 10/1990 | Ohkawa | 546/257 |
| 5,028,617 | 7/1991 | Lindel et al. | 514/332 |
| 5,130,437 | 7/1992 | Rocklage et al. | 546/261 |
| 5,216,134 | 6/1993 | Mukkala et al. | 534/15 |
| 5,252,740 | 10/1993 | Hale et al. | 546/263 |
| 5,324,825 | 6/1994 | Kankare et al. | 534/16 |
| 5,405,601 | 4/1995 | Dunn et al. | 424/9 |
| 5,457,186 | 10/1995 | Mukkala et al. | 534/15 |
| 5,559,214 | 9/1996 | Delecki et al. | 534/10 |
| 5,571,897 | 11/1996 | Takalo et al. | 534/15 |
| 5,608,059 | 3/1997 | Wear et al. | 540/465 |
| 5,624,907 | 4/1997 | Raymond et al. | 514/17 |

OTHER PUBLICATIONS

Clezy et al (1974), Aust. J. Chem., vol. 27, pp. 357–369, "The Chemistry of Pyrrolic Compounds. XXV. The Chemistry of Acetal and Thioacetal Derivatives of Pyrrolic Systems".

Berlin et al (1993), Liebigs Ann. Chem. No. 10, pp. 1153–1154, "Tripyrrlmethane als Bausteine zur Synthese Funktioneller Porphyrine".

Solomons, *Organic Chemistry,* 4th Ed., 1988, pp. 828–830.

Adolfsson et al., *J. Chem. Soc., Chem. Commun.* (14), pp. 1054–1055, 1992.

Adolfsson et al., *J. Chem. Soc., Chem. Commun.* (22), p. 1698, 1992.

*Primary Examiner*—Gary E. Hollinden
*Assistant Examiner*—Dameron Jones
*Attorney, Agent, or Firm*—James J. Mullen; Stuart D. Frenkel; John J. Piskorski

[57] ABSTRACT

Novel ligands for use in MRI contrast agents and which have the formula

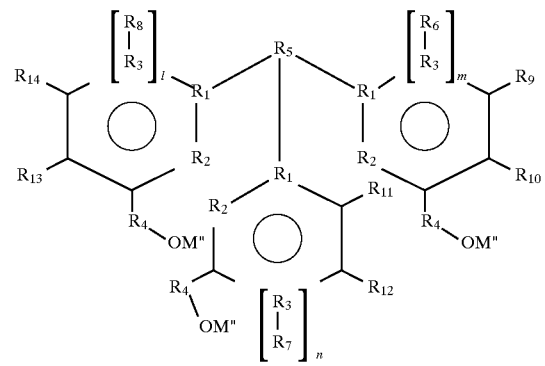

wherein $R_1$–$R_{14}$, M", l, m, and n are defined herein.

21 Claims, No Drawings

LIGANDS FOR MRI CONTRAST AGENT

FIELD OF THE INVENTION

This invention relates to magnetic resonance imaging (MRI), X-ray imaging, and radiopharmaceuticals. More particularly the invention relates to methods and compositions for enhancing MRI, X-ray imaging, and radiopharmaceuticals.

BACKGROUND OF THE INVENTION

The use of contrast agents in diagnostic medicine is rapidly growing. In X-ray diagnostics, for example, increased contrast of internal organs, such as the kidneys, the urinary tract, the digestive tract, the vascular system of the heart (angiography), and so forth is obtained by administering a contrast agent which is substantially radiopaque. In conventional proton MRI diagnostics, increased contrast of internal organs and tissues may be obtained by administering compositions containing paramagnetic metal species which increase the relaxation rate of surrounding protons. In ultrasound diagnostics, improved contrast is obtained by administering compositions having acoustic impedances different than that of blood or other tissues.

The recently developed technique of MRI encompasses the detection of certain atomic nuclei utilizing magnetic fields and radio-frequency radiation. It is similar in some respects to X-ray computed tomography (CT) in providing a cross-sectional display of the body organ anatomy with excellent resolution of soft tissue detail. As currently used, the images produced constitute a map of the proton density distribution, the relaxation times, or both, in organs and tissues. The technique of MRI is advantageously non-invasive as it avoids the use of ionizing radiation.

While the phenomenon of NMR was discovered in 1945, it is only recently that it has found application as a means of mapping the internal structure of the body as a result of the original suggestion of Lauterbur (*Nature*, 242, 190–191 [1973]). The fundamental lack of any known hazard associated with the level of magnetic and radio-frequency fields that are employed renders it possible to make repeated scans on vulnerable individuals. In addition to standard scan planes (axial, coronal, and sagittal), oblique scan planes can also be selected.

With an MRI experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin when placed in an applied magnetic field (B, expressed generally in units of gauss or Tesla [$10^4$ gauss]) align in the direction of the field. In the case of protons, these nuclei precess at a frequency, f, of 42.6 MHz, at a field strength of 1 Tesla. At this frequency, an RF pulse of radiation will excite the nuclei and can be considered to tip the net magnetization of the field direction, the extent of this rotation being determined by the pulse duration and energy. After the RF pulse, the nuclei "relax" or return to equilibrium with the magnetic field, emitting radiation at the resonant frequency. The decay of the emitted radiation characterized by two relaxation times, i.e., $T_1$, the spin-lattice relaxation time or longitudinal relaxation time, that is, the time taken by the nuclei to return to equilibrium along the direction the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thicknesses can be selected. This selection permits high quality transverse, coronal and sagittal images to be obtained directly, The absence of any moving parts in MRI equipment promotes high reliability. It is believed that MRI has a greater potential than CT for the selective examination of tissue characteristics in view of the fact that in CT, X-ray attenuation coefficients alone determine image contrast, whereas at least five separate variables ($T_1$, $T_2$, proton density pulse sequence and flow) may contribute to the MRI signal.

By reason of its sensitivity to subtle physiochemical differences between organs and/or tissues, it is believed that MRI may be capable of differentiating different tissue types in detecting diseases which induce physiochemical changes that may not be detected by X-ray or CT which are only sensitive to differences in the electron density of tissue.

As noted above two of the principal imaging parameters are the relaxation times, $T_1$ and $T_2$. For protons (or other appropriate nuclei), these relaxation times are influenced by the environment of the nuclei, (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of a given chemical compound is a function of the environment.

In general, paramagnetic species such as ions of elements with atomic numbers of 21 to 29, 42 to 44 and 58 to 70 have been found effective as MRI contrasting agents. Examples of suitable ions include chromium(III), manganese(II), manganese(III), iron(II), iron(III), cobalt(II), suitable ions include chromium(III), manganese(II), manganese(III), iron (II), iron(III), cobalt(II), nickel(II), copper(II), praseodymium(III), neodymium(III), samarium(III), and ytterbium(III). Because of their very strong magnetic moments, gadolinium(III), terbium(III), dysprosium(III), holmium(III) and erbium(III) are preferred. Gadolinium(III) ions have been particularly preferred as MRI contrasting agents.

Typically, paramagnetic ions have been administered in the form of complexes with organic complexing agents. Such complexes provide the paramagnetic ions in a soluble, non-toxic form, and facilitate their rapid clearance from the body following the imaging procedure. Gries et al., U.S. Pat. No. 4,647,447, disclose complexes of various paramagnetic ions with conventional aminocarboxylic acid complexing agents. A preferred complex disclosed by Gried et al. is the complex of gadolinium(III) with diethylenetriamine-pentaacetic acid ("DTPA"). Paramagnetic ions, such as gadolinium(III), have been found to form strong complexes with DTPA, ethylenediamine-tetraacetic acid ("EDTA"), and with tetraazacyclododecane-N,N', N",N'"-tetraacetic acid ("DOTA").

These complexes do not dissociate substantially in physiological aqueous fluids. The gadolinium complex of DTPA has a net charge of –2, whereas the gadolinium complex of EDTA or DOTA has a net charge of –1, and both are generally administered as soluble salts. Typical salts are sodium and N-methylglucamine. The administration of salt is attended by certain disadvantages. These salts can raise the in vivo ion concentration and cause localized disturbances in osmolality, which in turn, can lead to edema and other undesirable reactions.

Efforts have been made to design new ionic and neutral paramagnetic metals complexes which avoid or minimize the above mentioned disadvantages. In general, this goal can be achieved by converting one or more of the free carboxylic acid groups of the complexing agents to neutral, non-ionizable groups. For example, S. C. Quay, in U.S. Pat. Nos. 4,687,658 and 4,687,659, discloses alkylester and alkylamide derivatives, respectively, of DTPA complexes. Similarly, published Dean et al., U.S. Pat. No. 4,826,673 discloses mono- and polyhydroxy-alkylamide derivatives of DTPA and their use as complexing agents for paramagnetic ions. It can also be achieved by covalent attachment of organic cations of the complexing agent in such a manner that the sum of positive and negative charges in the resulting metal complex is zero.

The nature of additional substituents in the complexing agent can have a significant impact on tissue specificity. Hydrophilic complexes tend to concentrate in the interstitial fluids, whereas lipophilic complexes tend to associate with cells. Thus, differences in hydrophilicity can lead to different applications of the compounds. See, for example, Weinmann et al. AJR, 142, 679 (March 1984) and Brasch, et al. AJR, 142, 625 (March 1984).

Finally, toxicity of paramagnetic metal complexes is greatly affected by the nature of the complexing agents. In vivo release of free metal ions from the complex is a major cause of toxicity. Four principal factors are important in the design of chelates for making paramagnetic metal complexes that are highly stable in vivo and less toxic. The first three factors are thermodynamic in nature whereas the fourth involves chelate kinetics. The first factor is the thermodynamic stability constant of the metal-ligand. The thermodynamic stability constant indicates the affinity that the totally unprotonated ligand has for a metal. The second factor is the conditional stability constant which takes into account the pH and is important when considering stability under physiological pH. The selectivity of the ligand for the paramagnetic metal over other endogenous metal ions such as zinc, iron, magnesium and calcium is the third factor. In addition to the three thermodynamic considerations, complexes with structural features that make in vivo transmetallation reactions much slower than their clearance rates would be predicted to have low toxicities. Therefore, in vivo reaction kinetics are a major factor in the design of stable complexes. See, for example, Caheris et al., *Magnetic Resonance Imaging*, 8:467 (1990) and Oksendal, et al., *JMRI*, 3:157 (1993).

A need continues to exist for new and structurally diverse compounds for use as imaging agents. There is a further need to develop highly stable complexes with good relaxivity and osmolar characteristics.

Thus, there is always a need for new and more effective agents requiring lower dosage use, lower toxicity, higher resolution and more organ/disease specificity.

DESCRIPTION OF THE PRIOR ART

The following prior art references are disclosed for informational purposes.

U.S. Pat. No. 4,001,323 discloses water-soluble non-ionizing hydroxy-containing amide derivatives of 2,4,6-triiodoisophthalic acid for use as radiopaque materials.

U.S. Pat. No. 4,250,113 discloses new amides as X-ray contrast agents.

U.S. Pat. No. 4,396,598 discloses triiodoisophthalamide X-ray contrast agents.

U.S. Pat. No. 4,647,447 discloses new paramagnetic contrast agents.

U.S. Pat. No. 4,687,659 discloses homologs of diamide-DTPA-paramagnetic compounds as contrast agents for MR imaging.

U.S. Pat. No. 4,719,098 discloses enteral contrast medium useful for nuclear magnetic resonance imaging.

U.S. Pat. No. 4,885,363 discloses 1-substituted-1,4,7-triscarboxymethyl-1,4,7,10-tetraazacyclododecane useful when complexed with a paramagnetic metal atom as MR imaging agents.

U.S. Pat. No. 4,916,246 discloses paramagnetic chelates useful for NMR imaging.

U.S. Pat. No. 4,957,939 discloses sterile pharmaceutical compositions of gadolinium chelates useful as enhancing NMR imaging.

U.S. Pat. No. 5,405,601 discloses functionalized tripodal ligands for imaging applications.

*Proc. Natl. Acad. Sci.* U.S.A., Vol 93, pp 6610–6615, June 1996, Medical Sciences; Young et al. disclose gadolinium (III) texaphyrin: a tumor selective radiation sensitizer that is detectable by MRI.

H. Reimlinge, *Chem. Ber.,* 92, 970 (1995) discloses synthesis of substituted pyrazoles.

Kamitori Y. et al, *Heterocycles,* 38 (1), 21 (1994) discloses synthesis of substituted pyrazoles.

Sauer, D. R. et al., *Carbohyde Res.,* 241 (1993) 71 discloses synthesis of substituted pyrazoles.

Amoroso, A. J. et al, *J. Chem. Soc., Chem. Comm.* 1994, 2751, discloses a general synthesis of ligands.

Campbell, A. D. et al., *Aust. J. Chem.* 1971, 24, 377–83 discloses a general synthesis of ligands.

Kametani, T., *Tetrahedron,* 1970, 26, 5753 discloses a general synthesis of ligands.

All of the above cited prior art and any other references mentioned herein are incorporated herein by reference in their entirety.

SUMMARY OF THE INVENTION

The present invention provides novel compositions of matter having the formula

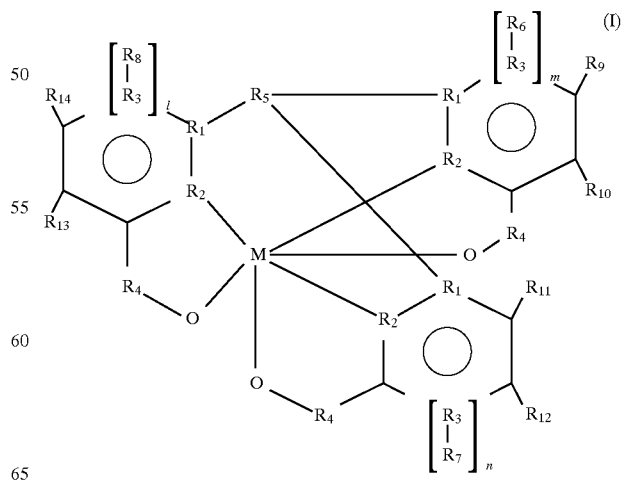

wherein $R_1$–$R_{14}$, M, l, m and n are defined herein and which have applications, for example, as MRI contrasting agents.

Compositions comprising the above formula (I) wherein M is a radioactive metal ion, a paramagnetic ion, or a metal ion capable of absorbing X-rays are also provided for use as radiopharmaceuticals, magnetic resonance imaging, and X-ray contrast agents, respectively.

Diagnostic compositions comprising the compounds of the invention are also provided. Methods of performing diagnostic procedures with compositions of the invention are also disclosed. The methods comprise administering to a patient an effective amount of the compositions of the invention and subjecting the patient to an imaging procedure.

DETAILED DESCRIPTION OF THE INVENTION

There is provided, in one part of the present invention, new and structurally diverse compositions of matter having the formula

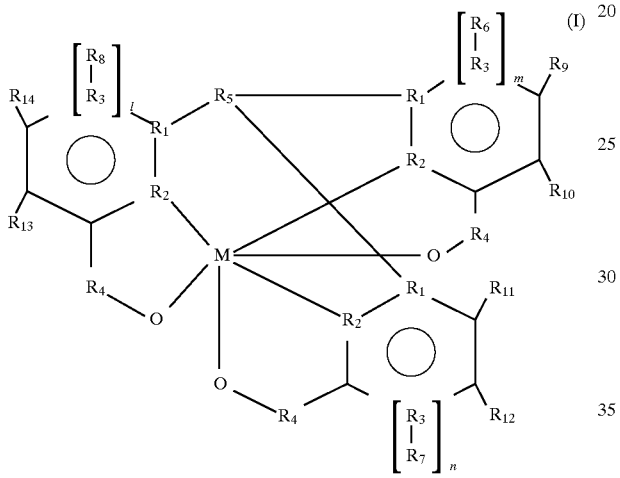

wherein:
l, m and n are independently 0 or 1
$R_1$ is C or N
$R_2$ is N, O, or S
$R_3$ is C
$R_4$ is CO, $SO_2$, $PO_2$—M', NH, or $CH_2$
$R_5$ is selected from the group consisting of
(a) P
(b) P=O
(c) $B(R)^-M'$
(d) N
(e) $N(CH_2)$
(f) $N[C(O)]_3$
(g) $N[CH_2C(O)]_3$
(h) CH
(i) COR
j) $COC(O)N(R)_2$
(k) $C(CH_2OR)(CH_2)_3$
(l) SiR
wherein R is selected from the group consisting of
(i) H
(ii) $C_1-C_{20}$ alkyl
(iii) hydroxyalkyl ($C_1-C_{20}$)
(iv) $CH_2CH(OH)CH_2(O\ CH_2CH(OH)CH_2)_nOH$ (n= 0–10)
(v) $CH_2CH_2(O\ CH_2CH_2)_nOH$ (n=0–10)
(vi) ribose
(vii) glucose
(viii) peptide or polypeptide
(ix) $PO_3^{2-}2M'$
and M' is $Na^+$ or meglumine $R_6-R_{14}$ are each independently selected from the group consisting of (a) R
(b) OR
(c) $N(R)_2$
(d) NHC(O)R
(e) $COO^-M'$
(f) $C(O)N(R)_2$
(g) $SO_3^-M'$ wherein R and M' are defined as above, and M is a suitable metal ion such as a metal ion of the lanthamide series having an atomic number of 57–70, or of a transition metal of an atomic number of 21–29, 42, or 44.

In the above formula I, M is selected from the group consisting of chromium(III), manganese(II), iron(III), iron (II), cobalt(II), nickel(II), copper(II), praseodymium(III), neodymium(III), samarium(III), ytterbium(III), gadolinium (III), terbium(III), dysprosium(III), holmium(III), erbium (III), lanthamium(III), gold(III), lead(II), bismuth(III), and europium(III).

Examples of suitable alkyl groups for use with the invention include methyl, ethyl, propyl, isopropyl, butyl, cyclohexyl, heptyl and octyl. Suitable alkoxy groups include methoxy, ethoxy, propoxy, butoxy, pentoxy, hexoxy, heptoxy and octoxy. Hydroxyalkyl groups suitable for use with the invention include both mono and poly hydroxyalkyls such as hydroxyethyl, 2-hydroxypropyl, 2,3-dihydroxypropyl, 2,3,4-trihydroxybutyl, tris (hydroxymethyl)methyl and 2-hydroxy-1-hydroxymethyl-ethyl. Suitable alkoxyalkyl groups include methoxymethyl, 2,3-dimethoxypropyl, tis(methoxymethyl)methyl, and 2-methoxy-1-methoxymethyl-ethyl.

An example of a class of compounds falling within formula (I) above include:

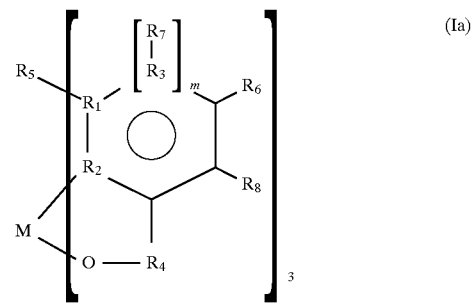

wherein $R_1-R_8$ and M have the same definition as in formula (I) above.

Examples of compounds falling within formula Ia include:

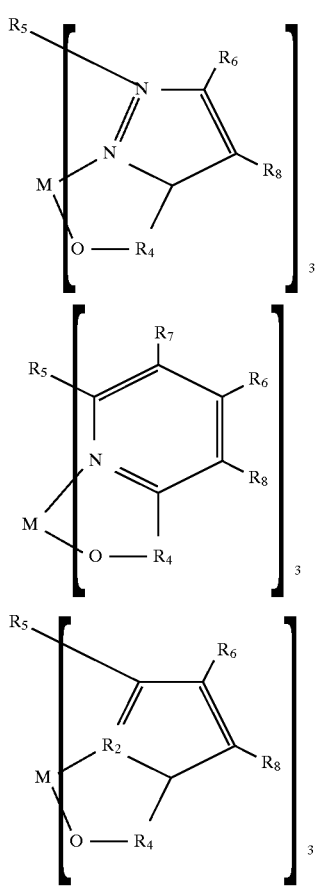

(II)

(III)

(IV)

wherein in formulae (II), (III), and (IV), $R_2$, $R_4$–$R_8$, and M have the same definition as set forth in formula (Ia).

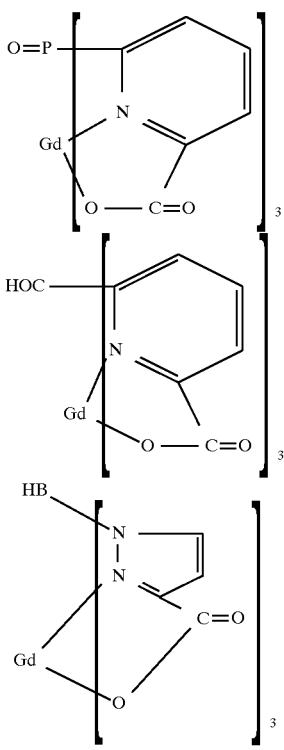

(V)

(VII)

(VIII)

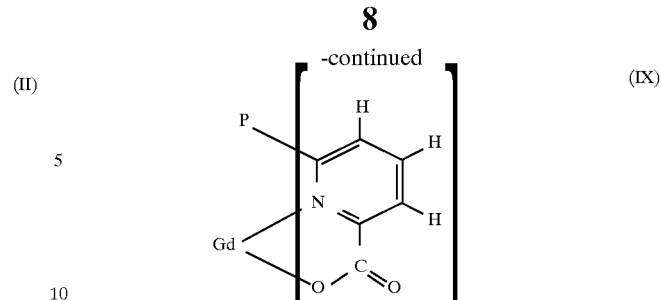

(IX)

The compositions of the present invention are suitable for use with a variety of modalities including X-rays, magnetic resonance imaging and radiopharmaceuticals.

The functionality of the $R_5$–$R_8$ groups of the compositions of the present invention afford the additional capability of derivatization to biomolecules and synthetic polymers. Biomolecule refers to all natural and synthetic molecules that play a role in biological systems. Biomolecules include hormones, amino acids, peptides, peptidomimetics, proteins, deoxyribonucleic acid (DNA) ribonucleic acid (RNA), lipids, albumins, polyclonal antibodies, receptor molecules, receptor binding molecules, monoclonal antibodies, a fragment of monoclonal antibody and aptamers. Specific examples of biomolecules include insulins, prostaglandins, growth factors, liposomes and nucleic acid probes. Examples of synthetic polymers include polylysine, arborols, dendrimers, cyclodextrins. The advantages of using biomolecules include enhanced tissue targeting through specificity and delivery. Coupling of the chelating moieties to biomolecules can be accomplished by several known methods (e.g., Krejacarek and Tucke *Biochem. Biophys. Rs. Comm.*, 30, 581 (1977); Hantowich, et al. *Science*, 220, 613 (1983). For example, a reactive moiety present in one of the $R_5$–$R_8$ groups is coupled with a second reactive group located on the biomolecule. Typically, a nucleophilic group is reacted with an electrophilic group to form a covalent bond between the biomolecule and the chelate. Examples of nucleophilic groups include amines, anilines, alcohols, phenols, thiols and hydrazines. Electrophilic group examples include halides, disulfides, epoxides, maleimeides, acid chlorides, anhydrides, mixed anhydrides, activated esters, imidates, isocyanates and isothiocyanates. And finally, the compositions of the invention should provide the additional advantage of being kinetically inert.

The present invention compositions with one or more central metal ions or metal ion equivalents (M), such as paramagnetic metals praseodymium(III), neodymium(III), samarium(III), ytterbium(III) terbium(III), dysprosium(III), holmium(III), erbium(III), iron(II), iron(III), chromium(III), cobalt(II) and nickel(II) are useful for enhancing magnetic resonance images. While such metal ions are themselves paramagnetic in nature and capable of altering the magnetic resonance signal characteristics of body tissues, organs or fluids, they may exhibit significant toxicity when administered in the form of ionic salts. However, the novel compositions of the present invention are relatively or substantially nontoxic and therefore useful for enhancing magnetic resonance images by favorably altering relaxation times $T_1$ and $T_2$ and affording improved contrast between normal and diseased tissues or organs.

The preferred compositions of the present invention are those formed with iron(II), iron(III), manganese(II), manganese(III) and gadolinium(III) as the central metal ion or ions (M). Depending upon the particular ligand ($R_5$) employed and the particular central metal ion used (M), the compositions formed may be neutral, ionic, cationic, or zwitterionic in nature, or they may be negatively charged.

The neutral compositions are generally preferred and generally appear to exhibit relatively lower toxicity as compared to ionic or negatively charged compositions. The negatively charged compositions formed by the ligands and central metal ions enumerated above may be further complexed with one or more cations of an inorganic or organic base which are physiologically tolerated. Examples of cations for further complexing include sodium, potassium, calcium, and salts of N-methylglucamine, and diethanolamine.

In addition to their utility in magnetic resonance imaging procedures, the compositions of the present invention can also be employed for delivery of either radiopharmaceuticals or heavy metals for X-ray contrast into the body. For use in diagnostic and therapeutic S radiopharmaceuticals the complexed metal ion (M) must be radioactive. Radioisotopes of the elements technetium, rhenium, indium, gallium, copper, ytterbium, samarium and holmium are suitable. For use as X-ray contrast applications the complexed metal ion (M) must be able to absorb adequate amounts of the X-rays. These metal ions are generally referred to as radiopaque. Suitable elements for use as the radiopaque metal ion include lead, bismuth, gadolinium, dysprosium, holmium and praseodymium.

The compositions of the present invention can be formulated into diagnostic compositions for enteral or parenteral administration. These compositions contain an effective amount of the paramagnetic ion complex along with conventional pharmaceutical carriers and excipients appropriate for the type of administration contemplated. For example, parenteral formulations advantageously contain a sterile aqueous solution or suspension of from about 0.05 to about 1.0M of a paramagnetic ion complex according to this invention. Parenteral compositions may be injected directly or mixed with a large volume parenteral composition for systemic administration. Preferred parenteral formulations have a concentration of paramagnetic ion complex of about 0.1M to about 0.5M. Such solutions also may contain pharmaceutically acceptable buffers and, optionally, electrolytes such as sodium chloride. The compositions may advantageously contain a slight excess (e.g., from about 0.01 to about 15.0 mole % excess) of a complexing agent or its complex with a physiologically acceptable, nontoxic cations. Such physiologically acceptable, non-toxic cations include calcium ions, magnesium ions, copper ions, zinc ions, salts of n-methylglucamine and diethanolamine, and the like. Generally, calcium ions are preferred.

Formulations for enteral administration may vary widely, as is well-known in the art. In general, such formulations are liquids which include an effective amount of the paramagnetic ion complex in aqueous solution of suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of NMR image. Such doses may vary widely, depending upon the particular paramagnetic ion complex employed, the organs or tissues which are subject of the imaging procedure, the NMR imaging procedure, the NMR imaging equipment being used, and the like. In general, parenteral dosages will range from about 0.001 to about 1.0 mmol of paramagnetic ion complex per kg of patient body weight. Preferred parenteral dosages generally range from about 0.01 to about 0.5 mmol of paramagnetic ion complex per kg of patient body weight. Enteral dosages generally range from about 0.5 to about 100 mmol, preferably from about 1.0 to about 10.0 mmol, preferably from about 1.0 to about 20.0 mmol of paramagnetic ion complex per kg of patient body weight.

The diagnostic compositions of the present invention are used in the conventional manner. The compositions may be administered to a patient, typically a warm-blooded animal, either systemically or locally to the organ or tissue to be imaged, and the patient then subjected to the NMR imaging procedure. Protocols for imaging and instrument procedures are found in texts such as Stark, D. D.; Bradley, W. G. *Magnetic Resonance Imaging;* Mosby Year Book: St. Louis, Mo., 1992.

Radiopharmaceutical Imaging Procedures are found in Fred A. Mettler, Jr., M.D., M.P.H., Milton J. Guiberteau, M.D., *Essentials of Nuclear Medicine Imaging,* Grune and Stratton, Inc., New York, N.T. 1983) and E. Edmund Kim, M.S., M.D. and Thomas P. Haynie, M.D., (MacMillan Publishing Co. Inc., New York, N.Y. 1987).

XRCM Imaging Procedures are found in Albert A. Moss, M.D., Gordon Gamsu, M.D., and Harry K. Genant, M.D., *Computed Tomography of the Body,* (W. B. Saunders Company, Philadelphia, Pa., 1992) and M. Sovak, Editor, *Radiocontrast Agents,* (Springer-Verlag, Berlin 1984).

In another facet of the present invention, there is provided new ligands which have application (after complexing with, for example, a paramagnetic ion) in the MRI area. These ligands have the general formula

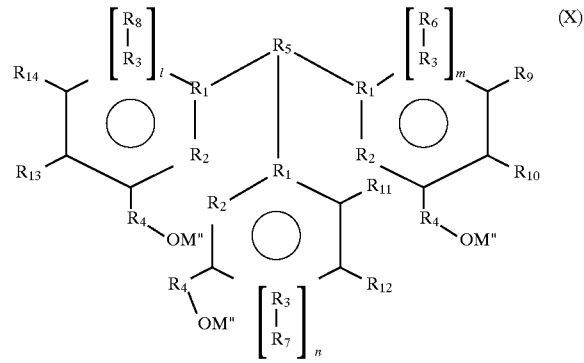

wherein $R_1-R_{14}$, l, m, and n are the same as set forth in formula (I) above, and M" is Na, Li, K, $NH_4^\oplus$, or MgBr.

A class of compounds (ligands) falling within formula (X) above are

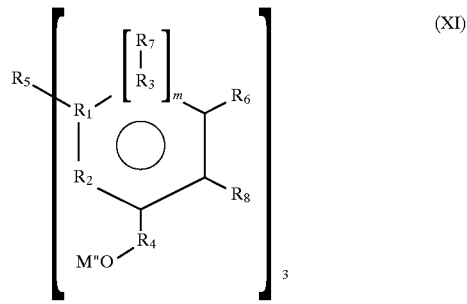

wherein $R_1-R_8$ and m are the same as set forth in formula (X) above, and M" is Na, Li, K, $NH_4^\oplus$, or MgBr.

Sub-generic ligand formulae under formula (XI) above have, for example, the following structural formulae:

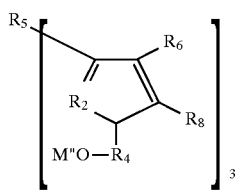
(XII)

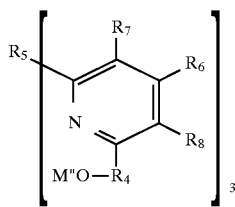
(XIII)

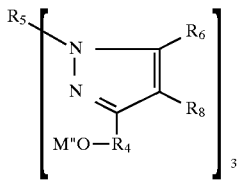
(XIV)

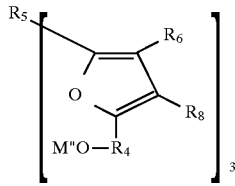
(XV)

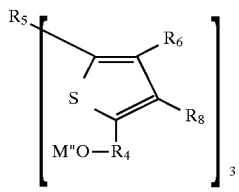
(XVI)

Examples of compounds falling within formula (XI) are as follows:

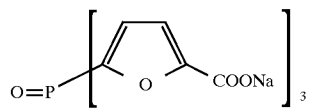
(XVII)

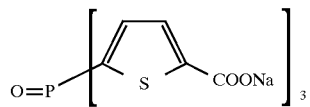
(XVIII)

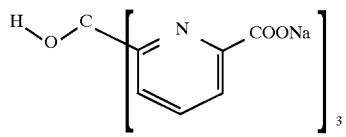
(XIX)

The novel ligands and the novel ligand-metal complexes of the present invention are prepared from substituted aromatic heterocycles ("SAH") which are generally commercially available from Aldrich Chemical Company (Milwaukee). The SAH have the general formula:

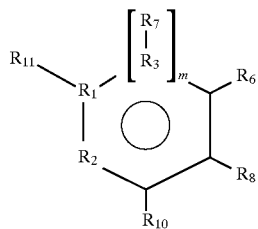

wherein $R_1$–$R_3$ and $R_6$–$R_8$, and m are defined above. $R_{10}$ and $R_{11}$ are defined below.

When m=1, these SAH are derivatives of pyridine in that $R_1$ and $R_3$=C, $R_2$=N, $R_{10}$=halogen or carboxylic group, and $R_{11}$=halogen.

When m=0, these SAH are derivatives of pyrazole in that $R_1$ and $R_2$ are both N, $R_{11}$=H, and $R_{10}$ is an ester of a carboxylic acid.

When m=0, these SAH are derivatives of furan or thiophene in that $R_1$=C, $R_2$ is O or S, $R_{10}$ is a halogen or carboxylic acid groups and $R_{11}$ is a halogen.

$R_6$–$R_8$ are the same as defined above and are protected if incompatible with the reaction conditions.

For example when m=1 and $R_2$ is N, both $R_{10}$ and $R_{11}$ can be halogen (such as Br) and then a halogen lithium exchange reaction is carried out at low temperature (e.g. from about −100° C. to about −20° C.) to generate a monolithium reagent, which is then coupled with a linking reagent such as POCl$_3$, PCl$_3$, or methyl chloroformate, to link three units of SAH to form a capping mode ligand in one or two steps as shown in Scheme 2. The other halogen atoms on the SAH are replaced in order to introduce the M'O—$R_4$ group in one or more steps, also show in Scheme 2.

In another example where m=o and the starting material is either a furan or a thiophene and where $R_{10}$ is a carboxylic acid and $R_{11}$ is halogen, $R_{10}$ is first protected by converting it to an oxazoline under amidation conditions as shown in Scheme 1, then, the amide is thus subjected to ring closure conditions to form the oxazoline. A halogen lithium exchange reaction is then carried out at low temperature to form a monolithium reagent which is coupled with a linking agent such as POCl$_3$, PCl$_3$ or methyl chloroformate, to link three units of SAH. The carboxylic acid groups are then regenerated as shown in Scheme 1 by cleaving the oxazoline.

When the starting material is a pyrazole derivative, the coupling reaction with the linking reagent is carried out by refluxing the SAH with the linking reagent in a solvent in the presence of a base. In this case, the SAH is used in excess.

The final step in the overall synthesis for preparing the ligand-metal complex is reaction of the novel ligand with a solution containing the metal ion in the form of a compound which, for example, may be the acetate form, e.g. Gd(OAc)$_3$. Pressures and temperatures are not critical. The mole ratio of ligand to metal (atom) is about 1:1.

Some examples of specific processes for preparing the novel compositions of the present invention are set forth in Schemes 1 and 2 and which, respectively, outline the detailed procedures described in Examples 1–5, and Examples 13–17.

SCHEME 1
Synthesis of Gadolinium Tris(5-carboxy-2-furanyl)phosphine oxide (GDTCFPO)

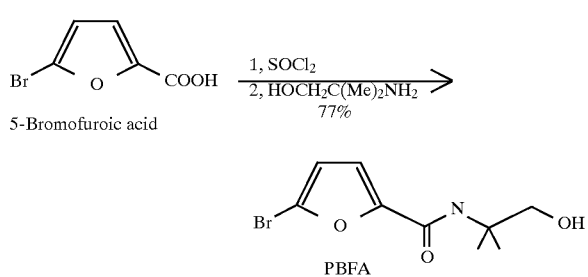
5-Bromofuroic acid
1, SOCl₂
2, HOCH₂C(Me)₂NH₂
77%

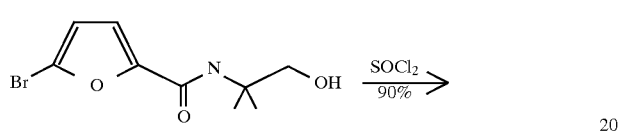
PBFA
SOCl₂
90%

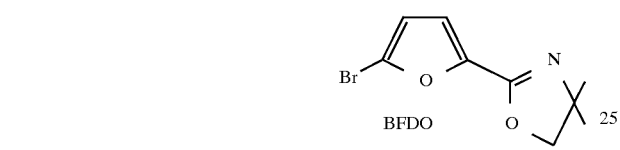
BFDO

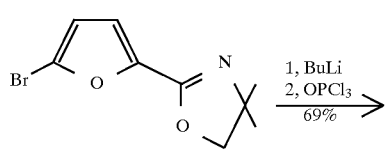
1, BuLi
2, OPCl₃
69%

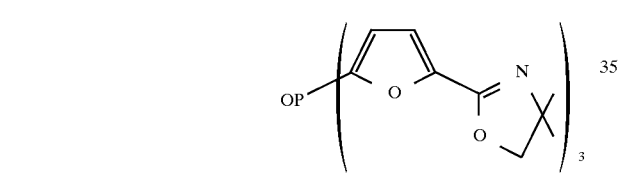
TOFPO

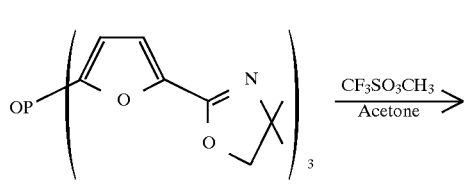
CF₃SO₃CH₃
Acetone

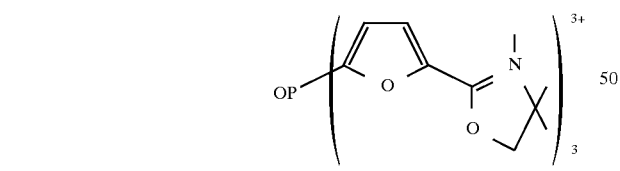

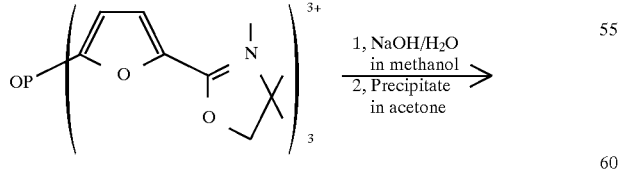
1, NaOH/H₂O in methanol
2, Precipitate in acetone

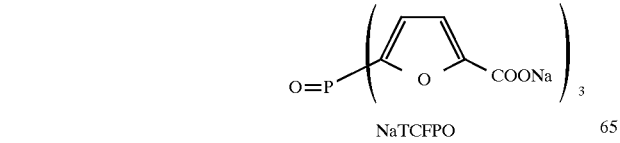
NaTCFPO

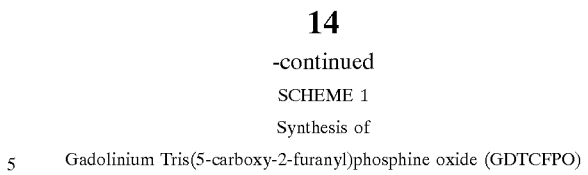
Gd(OAc)₃

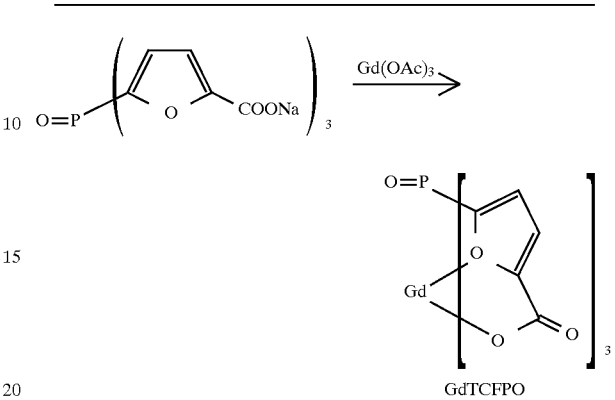
GdTCFPO

SCHEME 2
Synthesis of Gadolinium Tris(2-carboxy-6-pyridyl)methanol (GdTCPM)

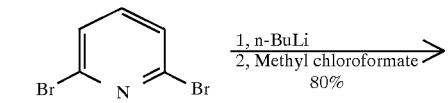
1
1, n-BuLi
2, Methyl chloroformate
80%

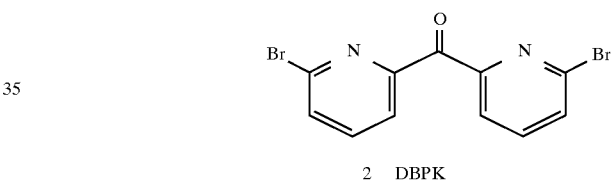
2  DBPK

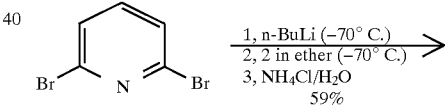
1, n-BuLi (−70° C.)
2, 2 in ether (−70° C.)
3, NH₄Cl/H₂O
59%

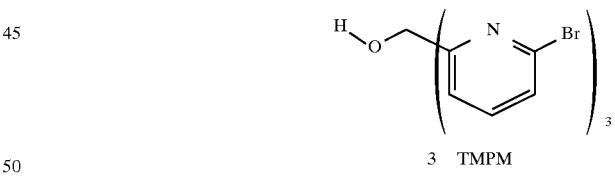
3  TMPM

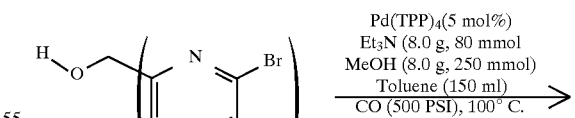
4.0 g, 8.0 mmol
Pd(TPP)₄ (5 mol%)
Et₃N (8.0 g, 80 mmol)
MeOH (8.0 g, 250 mmol)
Toluene (150 ml)
CO (500 PSI), 100° C.

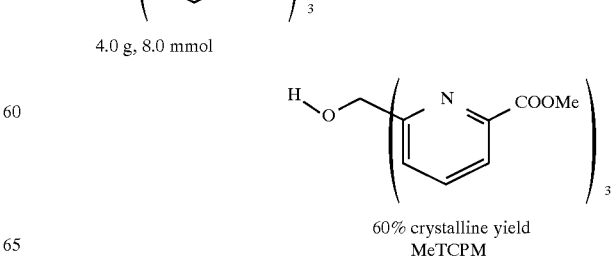
60% crystalline yield
MeTCPM

-continued
SCHEME 2
Synthesis of
Gadolinium Tris(2-carboxy-6-pyridyl)methanol (GdTCPM)

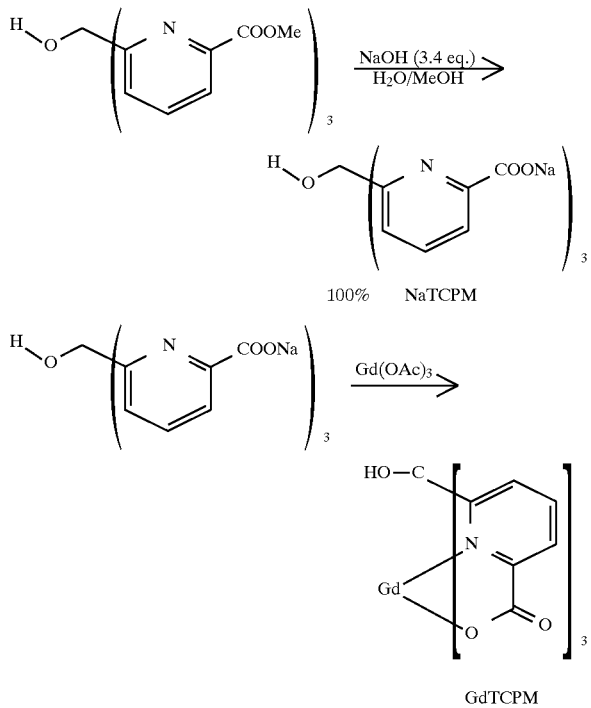

GdTCPM

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLES

Example 1

Synthesis of N-(2-methyl-1-hydroxy)isopropyl2-bromo-5-furamide

5-Bromofuric acid (50 g, 0.262 mol) was charged into a three neck Schlenk flask equipped with a thermocouple temperature probe and a condenser, which was sealed with a stopper. The setup was evacuated with high vacuum for 30 minutes and then refilled with nitrogen. Thionyl chloride (250 ml) was added by removing the temperature probe temporarily. The stopper on the condenser was replaced with a T-joint, which was connected on one end to nitrogen and the other end to a $NaOH/H_2O$ trap. An empty trap should also be placed between the T joint and the base trap to prevent the base from being sucked into the reaction flask in the event of a pressure drop in the reaction flask. A gentle flow of nitrogen gas was maintained through the T and vented from the trap. The valve on the side arm of the flask was turn off and cooling water turned on. Set the temperature controller to 80° C. and refluxed the solution for an hour. Thionyl chloride was then removed by partial vacuum distillation. Toluene was added, and then removed to remove thionyl chloride completely to obtain a solid. The solid was dissolved in 150 ml methylene chloride and cooled with an ice bath. 2-Amino-2-methylpropanol (23.35 g, 0.278 mol) and triethylamine (39 ml, 0.278 mol) in $CH_2Cl_2$ (100 ml) was added dropwise. The resulting dark solution was allowed to warm to room temperature and stirred for two more hours. Methylene chloride was then removed and residue dissolved in 500 ml of ethyl acetate and cooled with an ice bath. Potassium carbonate (40 g, 0.29 mol) in 70 ml of water was added. Layers were separated and aqueous layer was extracted with ethyl acetate (2×100). Combined ethyl acetate solution was washed with 200 ml of saturated NaCl solution, dried with $Na_2SO_4$, and filtered. The filtrate was evaporated to obtain an oil. The crude oil was stirred in toluene (90 ml) and hexane (30 ml) to obtain a solid, which was recrystallized by dissolving in hot (about 60° C.) toluene (90 ml) and hexane (30 ml) to yield 48 g (70%) pure product. $^1H$ NMR ($CDCl_3$, δ, TMS):1.4(s, 6H), 3.7 (s, 2H), 6.3 (bs, 1H), 6.4(d, $J_{H-H}$=3.5 Hz, 1H), 7.0(d, $J_{H-H}$=3.5 Hz, 1H). $^{13}C$ NMR($CDCl_3$,δ,TMS):24.6, 56.5, 70.2, 114.3, 116.8, 124.4, 149.5, 157.6.

Example 2

Synthesis of 2-(2-bromo-5-furanyl)-4,4-dimethyloxazoline (BFDO)

The amide (30 g, 0.114 mol) obtained from Example 1 was charged into a 250 ml Schlenk flask equipped with an addition funnel and a stir bar. The setup was evacuated for 30 minutes and refilled with nitrogen. $SOCl_2$ (30 ml, 47.6g) was added into the addition funnel. A T-joint, connected to nitrogen on one end and a base trap on the other end, was used to cap the addition funnel with a gentle flow of nitrogen through the T-joint. $SOCl_2$ was then added to the reaction flask and stirring started. Reaction started immediately, generating bubbles. The addition took about 10 minutes. The solution was stirred for an additional 30 minutes and then poured into 150 ml of dry ether to precipitate the product. The white precipitate was filtered, washed with 50 ml of ether and air dried. The white powder was then stirred in 40 ml of 20% NaOH water solution for 30 minutes. Ether (150 ml) was then added and stirring continued. All the solid dissolved in about 10 minutes. Layers were then separated and aqueous layer extracted with 50 ml of ether. Ether layers were combined, dried with $K_2CO_3$ for one hour, and filtered. Ether was removed under vacuum to obtained a white solid. Yield, 24.9 g, 90%. $^1H$ NMR ($CDCl_3$, δ, TMS):1.4(s, 6H), 4.1(s, 2H), 6.4(d, $J_{H-H}$=3.3 Hz, 1H), 6.9(d, $J_{H-H}$=3.3 Hz, 1H). $^{13}C$ NMR ($CDCl_3$,δ, TMS):28.1, 67.8, 79.2, 113.3, 116.2, 125.7, 144.8, 153.4.

Example 3

Synthesis of tris(5-(4,4-dimethyl-2-oxazolinyl)-2-furanyl)phosphine oxide (TOFPO)

N-Butyllithium (100 ml, 0.16 mol, 1.6M in hexanes) was added dropwise with stirring to a cold (−45° C.) solution of BFDO (39.0 g, 0.16 mol) in 160 ml of THF. Upon finishing addition, the solution was warmed to −10° C. for 5 minutes and then cooled back to −45° C. $OPCl_3$ (8.0 g, 0.052 mol) in 30 ml of THF was added dropwise. The solution was allowed to warm to room temperature and stirred at room temperature for 30 minutes. Solvents were then removed and residue dissolved in 200 ml of methylene chloride. Water (200 ml) was then added and the resulting cloudy solution transferred into a separation funnel. Methylene chloride layer was collected and aqueous layer extracted with methylene chloride (100 ml). Combined methylene chloride solution was washed with 300 ml of brine and then dried with $Na_2SO_4$ for 3 hours. The solution was filtered and methylene chloride was removed from filtrate to obtain 6.0 g of brown powder. This brown powder was recrystallized by dissolving in hot (60° C.) toluene and then cooling the solution to −20° C. to yield 21.7 g, 77% product. $^1$H NMR (CDCl$_3$, δ,TMS):1.4(s, 18H), 4.1(s, 6H), 7.1(dd, $J_{H-H}$=3.5 Hz, $J_{H-P}$=1.6 Hz, 3H), 7.3(dd, $J_{H-H}$=3.5 Hz, $J_{H-P}$=1.6 Hz, 3H). $^{13}$C NMR (CDCl$_3$, δ,TMS): 28.1, 68.2, 79.2, 114.7(d, $J_{C-P}$=9.1 Hz), 125.4 (d, $J_{C-P}$=21.0 Hz), 147.2 (d, $J_{C-P}$=155 Hz), 149.2 (d, $J_{C-P}$=9.4 Hz), 153.7. $^{31}$P NMR (CDCl$_3$, δ, H$_3$PO$_4$): −12.5. H NMR indicated that the product was contaminated with the starting material BFDO. LC/APCI/MS: mn/e, 540 (M+H) and small peak at 244 (BFDO M+H).

Example 4

Synthesis of sodium tris(5-carboxy-2-furanyl)phosphine oxide (NaTCFPO)

TOFPO (9.0 g, 16.7 mmol) was dissolved in 200 ml of acetone and cooled to −20° C. Methyl triflate (8.31 g, 50.6 mmol) was added dropwise. Acetone was removed after the solution was allowed to warm to room temperature to obtain 17.4 g of brown solid.

The brown solid was dissolved in 130 ml of methanol and cooled with an ice bath. NaOH (50%, 13.5 g, 0.17 mol), diluted with 15 ml of water, was added dropwise. The resulting solution was stirred for 2 hours at room temperature and then stirred into 1.2 liters of acetone to precipitate the product. The precipitate was filtered and it started to absorb moisture from air very quickly. It was dissolved in small amount of methanol and transferred into flask and dried under vacuum to yield 6.7 g of crude product which contained methanol and small amount of faroic acid, which is most likely produced from BFDO. $^1$H NMR (CDCl$_3$,δ, TMS): 7.0 (m); $^{13}$C NMR (CDCl$_3$, δ, TMS): 115.3 (d, $J_{C-P}$=8.6 Hz), 120.7 (d, $J_{C-P}$=21.0 Hz), 153.4 (d, $J_{C-P}$=7.8 Hz), 153.6 (d, $J_{C-P}$=176 Hz), 166.4. $^{31}$P NMR (CDCl$_3$, δ, H$_3$PO$_4$): −2.2. LC/APCI/MS (95% methanol/5% water): m/e 403 (M−2Na+3H).

Example 5

Synthesis of gadolinium tris(5-carboxy-2-furanyl) phosphine oxide (GdTCFPO)

Gd(OAc)$_3$XH$_2$O (FW:458, 0.10 g, 0.22 mmol) in 5 ml of water was added to a solution of NaTCFPO (0.11 g, 90% purity, 0.22 mmol) in 5 ml of water with stirring. LC analysis of a sample taken after 30 minutes showed that gadolinium complex was formed. Pure solid product was isolated by reducing the volume, addition of ethanol and then cooling to 0° C.; the product had the structural formula shown below:

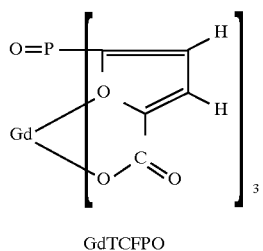

GdTCFPO

Example 6

Preparation of tris(6-bromo-2-pyridyl)phosphine (TBPP)

A reaction flask was equipped with a mechanical stirrer, nitrogen purge, internal temperature probe, and two equalizing addition funnels. The flask was charged with diethyl ether (450 mL) and 2,6-dibromopyridine (55.8 g, 0.235 mol, MW 237, 5 equiv) and the resultant slurry was cooled to −75° C. with agitation. One addition funnel was charged with n-butyllithium solution in hexane (120 mL, 1.6M, 0.192 mol, 4 equiv) and the butyllithium was added to the reaction mixture with agitation at such a rate that the internal reaction temperature was maintained at −70° to −75° C. After the addition was complete the reaction temperature was maintained at −75° C. for an additional 30–60 min.

The second addition funnel was charged with diethyl ether (50 mL) and phosphorus trichloride (6.6 g, 0.048 mol, MW 137.3, 1.00 equiv). The phosphorus trichloride solution was added to the reaction mixture with agitation at such a rate that the internal reaction temperature was maintained at −70° to −75° C. After the addition was complete the reaction temperature was maintained at −75° C. for an additional 30–60 min.

The reaction was quenched by the dropwise addition of methanol (6 mL) at −75° C. The reaction was gradually warmed to −20° C., then aqueous 2 N HCl (30 mL) was added at −20° C.

The precipitated solids were isolated by filtration and washed with diethyl ether (100 mL), demineralized water (100 mL), and diethyl ether (100 mL). The crude solids were dried in vacuo to afford 23.69 g of off-white powder (24.1 g theoretical yield, 96% by HPLC area %). $^1$H NMR (CDCl$_3$, δ, TMS): 7.4(m, 2H), 7.5(m, 1H) ppm. $^{13}$C NMR (CDCl$_3$, δ, TMS): 127.8, 128.4 d, 138.1 d, 142.6, 162.3 d ppm. $^{31}$P NMR (CDCl$_3$, δ, H$_3$PO$_4$): 0.26 ppm. LC/APCI/MS (90% acetonitrile, 10% water): m/e 502+504 (M+H$^+$).

Example 7

Preparation of tris(6-cyano-2-pyridyl)phosphine (TCNPP)

A flask was equipped with a reflux condenser, agitator, nitrogen purge and heat source. The flask was charged copper (I) cyanide (20.27 g, 0.226 mol, MW 89.5, 5.4 equiv) in dry pyridine (120 mL). Finely powdered tris(6-bromo-2-pyridyl)phosphine (20.91 g, 0.042 mol, MW 502, 1.0 equiv) from Example 6 was added to the reaction flask with vigorous agitation. The reaction mixture was heated at reflux for 12 hr. The heat source was removed and the reaction mixture cooled to ice bath temperature. Saturated aqueous sodium cyanide (60 g NaCN/160 mL water) was added to the cooled reaction and the mixture was stirred for 4 hr at ice bath temperature. The solids were isolated by filtration and washed with water (5×40 mL) followed by methanol (5×40 mL) until the washes were colorless. The crude solids were dried in vacuo to afford 11.0 g of brown solids (14.2 g theoretical yield, 88% by HPLC area %). $^1$H NMR (CDCl$_3$, TMS): 7.7 (d, $J_{H-H}$=7.3 Hz, 1H), 7.8 (m, 2H) ppm. $^{13}$C NMR (CDCl$_3$, TMS): 116.7 128.1, 132.7 d, 134.6 d, 136.9, 162.4 ppm. $^{31}$P NMR (CDCl$_3$, H$_3$PO$_4$): 2.7 ppm. LC/APCI/MS (90% acetonitrile, 10% water): m/e 341 (M+H$^+$).

Example 8

Preparation of tris(6-carboxy-2-pyridyl)phosphine hydrochloride (TCPP·HCl)

A reaction flask was equipped with a reflux condenser, agitator and a nitrogen purge. The flask was charged tris(6-cyano-2-pyridyl)phosphine (10.27 g, 30 mmol, MW 340, 1.0 equiv) from Example 7 and concentrated HCl (350 mL, d1.2=420 g, 37% HCl=155 g HCl, MW 36.5, 4.3 mol, ca. 140 equiv) was carefully added with agitation. The resultant dark brown solution was heated at 60° C. for 18 hr.

The reaction mixture was concentrated by evaporation at below 60° C. and the residue was treated several times with chloroform (2×50 mL) followed by concentration to azeotropically remove water to afford 20.2 g of crude product as a brown solid.

The crude tris(6-carboxy-2-pyridyl)phosphine (19.92 g) was quickly dissolved and filtered in warm demineralized water (130 mL). The filtrate was allowed to stand at ambient temperature for 2 hr, then the precipitated solids were isolated by filtration. The solids were washed with cold demineralized water then dried the in vacuo to afford 10.14 g of light brown solids (12.0 g theoretical yield for tris hydrochloride, 94% by HPLC area %). $^1$H NMR (DMSO-d$_6$, δ, TMS): 7.4(d, $J_{H-H}$=7.6 Hz, 1H), 7.9(m, 1H), 8.0 (d, $J_{H-H}$=7.7 Hz, 1H)ppm. $^{13}$C NMR (DMSO-d$_6$, δ, TMS): 125.1, 132.3 d, 138.7, 149.9 d, 161.9, 166.6 ppm. $^{31}$P NMR (DMSO-d$_6$, δ, H$_3$PO$_4$): −3.2 ppm.

Example 9

Preparation of tris(6-carboxy-2-pyridyl)phosphine sodium salt (TCPP·Na)

An Erlenmeyer flask was immersed in an 80° C. water bath then charged with tris(6-carboxy-2-pyridyl)phosphine hydrochloride (Example 8) (3.11 g, MW 506.5 for 3 HCl, 6.1 mmol). Saturated aqueous sodium bicarbonate solution (22.5 mL, ca. 10 wt %=2.25 g NaHCO$_3$, MW 84, 27 mmol, 4.4 equiv) was added to the flask dropwise at ambient temperature. The resultant dark red-brown solution was hot filtered and the filtrate was slowly cooled to ambient temperature, followed by cooling to ice bath temperature. The slurry was held at ice bath temperature for 1 hr and the solids were isolated by filtration and washed with cold demineralized water. The solids were dried in vacuo to afford 1.57 g of light pink flakes (2.84 g theoretical yield for tris sodium salt, 95% by HPLC area %). $^1$H NMR (D$_2$O, δ, TMS): 7.1 (d, $J_{H-H}$=7.4 Hz, 1H), 7.8 (m, 2H) ppm. $^{13}$C NMR (D$_2$O, δ, TMS): 123.9, 130.9, 138.8, 155.4 d, 159.8, 173.1 ppm. $^{31}$P NMR (D$_2$O, δ, H$_3$PO$_4$): −5.9 ppm. LC/ESI/MS (50:50 aqueous HOAc:MeOH): m/e 420 (M−2Na$^+$+3H$^+$).

Example 10

Preparation of tris(6-carboxy-2-pyridyl)phosphine gadolinium complex (GdTCPP)

A reaction flask was equipped with a reflux condenser, agitator, addition funnel, nitrogen source and heating bath. The tris(6-carboxy-2-pyridyl)phosphine sodium salt (310 mg, 0.67 mmol, MW 463) from Example 9 was dissolved warm demineralized water (10 mL) and the resultant solution was filtered and charged to reaction flask. Gadolinium (III) acetate (260 mg, 0.64 mmol, MW 406 for tetrahydrate, 1 equiv) was dissolved in warm demineralized water (10 mL) and the resultant solution was filtered and charged to the addition funnel. The bath was heated to 90° C. and the gadolinium acetate solution was added dropwise with agitation over 30 min. Once the addition was complete, the reaction was cooled to ambient temperature and the white solids were isolated by filtration and washed with demineralized water. The solids were dried in vacuo to afford 130 mg of white solids (369 mg theoretical yield for anhydrous complex, 93% by HPLC area %), and having the structural formula shown below:

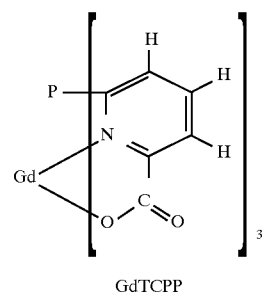

GdTCPP

Example 11

Preparation of tris(6-carboxy-2-pyridyl)phosphine oxide sodium salt (TCPPO·Na)

An Erlenmeyer flask was charged with tris(6-carboxy-2-pyridyl)phosphine hydrochloride (3.03 g, 6.0 mmol, MW 506.5 for trihydrochloride, 1.0 equiv) from Example 8 and acetonitrile (210 mL) and immersed in a heating bath warmed to 80° C. In order to completely dissolve the solids, demineralized water (30 mL) was added to the warmed mixture. Once the solids dissolved the mixture was hot filtered and allowed to cool to ambient temperature. Aqueous 10% hydrogen peroxide (6 mL, 0.60 g H$_2$O$_2$, 17.6 mmol, MW 34, 3 equiv) was added to the cooled filtrate and the reaction was allowed to stand at ambient temperature overnight.

The reaction was concentrated to near dryness in vacuo at <40° C. The residual solids were triturated with demineralized water (30 mL). After decantation, the water wet solids were dissolved in aqueous sodium bicarbonate at 80° C. (50 mL). The solution was hot filtered and the filtrate was cooled to ambient temperature. The precipitated solids were isolated by filtration and washed with a minimum amount of cold demineralized water. The solids were dried in vacuo to afford 2.81 g of white flakes (2.87 g theoretical yield for tris sodium salt, 89% by HPLC area %). $^1$H NMR (D$_2$O, δ,TMS): 8.0 (bs, 2H), 8.1 (bs, 1H) ppm. $^{13}$C NMR (D$_2$O, δ, TMS): 126.9, 129.3 d, 139.1, 151.1 d, 154.8 d, 171.5 ppm. $^{31}$P NMR (D$_2$O, δ, H$_3$PO$_4$): 4.3 ppm. LC/ESI/MS (50:50 aqueous HOAc:MeOH): m/e 436 (M−2Na$^+$+3H$^+$).

Example 12

Preparation of tris(6-carboxy-2-pyridyl)phosphine oxide gadolinium complex (GdTCPPO)

A reaction flask was equipped with a reflux condenser, agitator, addition funnel, nitrogen source and heating bath. The tris(6-carboxy-2-pyridyl)phosphine oxide sodium salt (310 mg, 0.65 mmol, MW 479) from Example 11 was dissolved warm demineralized water (10 mL) and the resultant solution was filtered and charged to reaction flask. Gadolinium (III) acetate (250 mg, 0.62 mmol, MW 406 for tetrahydrate) was dissolved in warm demineralized water (10 mL) and the resultant solution was filtered and charged to the addition funnel. The bath was heated to 90° C. and the gadolinium acetate solution was added dropwise with agitation over 30 min. Once the addition was complete, the reaction was cooled to ambient temperature and the white solids were isolated by filtration and washed with demineralized water. The solids were dried in vacuo to afford 100 mg of white solids (367 mg theoretical yield for anhydrous complex), and which had the following structural formula:

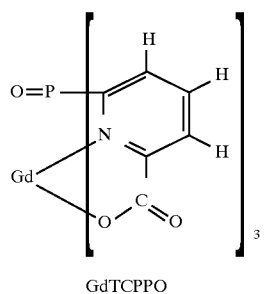

GdTCPPO

Example 13

Synthesis of bis(2-bromo-6-pyridyl)ketone (BBPK)

2,6-Dibromopyridine (38 g, 0.16 mol.) was charged into a 1 liter, 4-neck flask equipped with a stir bar, a temperature probe, a gas inlet w/stopcock, a septum(wired onto center neck), and an addition funnel (125 ml). Dry ether (400 ml) was added to the flask and methyl chloroformate (6.8 g, 0.07 mol.) in 40 ml ether was charged into the addition funnel. The flask was taken out of the glovebox to a bench and placed under $N_2$ atmosphere. The flask was chilled to below $-70°$ C. with $CO_2$/acetone and n-butyllithium (100 ml, 0.16 mol., 1.6M in hexanes) was added dropwise via a cannula. The addition took over 30–45 minutes. The solid 2,6-dibromopyridine dissolved and the solution turned yellow as n-butyllithium was added. The solution was stirred for one hour after the addition completed, maintaining the temperature at $-70°$ C. or below. The resulting yellow solution was sampled at this time to verify that the reaction was complete, quenching an aliquot into methanol and injecting the solution into an HPLC. Methyl chloroformate was then added dropwise over 20 minutes. A burgundy-purple solution was obtained and stirred for one hour. Methanol (13 ml) was then added to quench any unreacted lithium reagent and the solution was allowed to warm to $-10°$ C. The solution was then quenched with a solution of $NH_4Cl$ (4.7 g, 0.09 mol) in 20 ml of $H_2O$ and stirred until the solution reached room temperature. The pinkish-beige slurry was filtered through sintered glass funnel and washed with ether. The solid was then reslurried in 50 ml $H_2O$ and filtered again. The resulting solid was dried overnight in 60° C. vacuum oven to give 19.2 g.(0.056 mol, 80% yield) of BBPK. $^1$H NMR ($CDCl_3$, δ,TMS): 7.67(d, $J_{H-H}$=7.8 Hz), 7.75(t, $J_{H-H}$=7.8 Hz), 8.06 (d, $J_{H-H}$=7.8 Hz). $^{13}$C NMR ($CDCl_3$, δ, TMS): 124.2, 131.3, 138.9, 141.4, 154.0, 189.1. LC/APCI/MS: n/e, 341 (M+H$^+$).

Example 14

Synthesis of tris(2-bromo-6-pyridyl))methanol (TBPM)

In a glove box, BBPK (10 g, 0.029 mole) (Example 13) and 75 ml ether was charged into a 250 ml 2-neck Schlenk flask equipped with a stir bar, a septum, and a temperature probe adapter. Separately, 2,6-dibromopyridine (7.13 g, 0.03 mol) and 75 ml ether was charged into another 250 ml Schlenk flask equipped with an addition funnel containing n-butyllithium (18.75 ml, 0.03 mol, 1.6M in hexanes) and a temperature probe adapter. Both flasks were taken out of the box, placed under $N_2$ and cooled to $-70°$ C. while stirring n-Butyl lithium was added over 30 minutes and the slurry was stirred until all the solid dissolved. The addition funnel was then replaced with a rubber septum under nitrogen. The resulting lithium reagent was transferred quickly via a cannula to the flask containing the ketone slurry with stirring at $-70°$ C. The resulting homogeneous dark-blue solution was stirred at $-70°$ C. for an additional hour, quenched with 3 ml of methanol, and then allowed to warm up. The solution, which became greenish yellow at about $-55°$ C., was quenched with 1.6 g (0.03 mol) of $NH_4Cl$ in 15 ml $H_2O$ at $-10°$ C. The resulting slurry was warmed to room temperature, filtered and washed with ether and then water. The solid was reslurried in cold $H_2O$, filtered and dried to yield 8.35 g (0.017 mol, 59% yield) of beige solid product. $^1$H NMR ($CDCl_3$, δ, TMS): 7.41(d, $J_{H-H}$=7.7 Hz), 7.58 (t, $J_{H-H}$=7.7 Hz), 7.69 (d, $J_{H-H}$=7.7 Hz). $^{13}$C NMR ($CDCl_3$, δ, TMS): 79.7, 121.4, 126.6, 138.5, 139.4, 162.2. LC/APCI/MS : m/e, 498 (m+H$^+$).

Example 15

Synthesis of methyl tris(2-carboxy-6-pyridyl))methanol (MeTCPM)

A solution was prepared under nitrogen containing TBPM (4.0 g, 8.0 mmol) (Example 14), Pd(PPh$_3$)$_4$ (0.46 g, 0.4 mmol) (Example 14), NEt$_3$ (8.0 g, 79 mmol), methanol (8.0 g, 250 mmol) and toluene (150 ml). This solution was transferred into a 300 ml stainless steel Parr reactor which was purged with nitrogen. The reactor was purged three times with carbon monoxide (CO), pressurizing to 500 psi and then releasing the pressure. It was then pressurized to 500 psi with CO, heated to 100° C. and stirred at 500 RPM. The reaction was run for 72 hours. After allowing the reactor to cool to room temperature, it was depressurized and purged with nitrogen. The solution was filtered to remove salt produced and the filtrate was evaporated. The residue was dissolved in toluene and filtered. The filtrate was evaporated to yield an orange oil. The product was purified by recrystallization from methanol. Yield: 2.1 g, 60%. $^1$H NMR ($CDCl_3$, δ, TMS): 3.89 (s, 9H), 7.82 (t, $J_{H-H}$=7.8 Hz, 3H), 7.99(d, $J_{H-H}$=7.8 Hz, 3H), 8.11(d, $J_{H-H}$=7.8 Hz, 3H). $^{13}$C NMR ($CDCl_3$, δ, TMS): 52.5, 80.9, 123.9, 126.7, 137.2, 145.9,162.1, 165.5. LC/APCI/MS: m/e 438 (M+H).

Example 16

Synthesis of sodium tris(2-carboxy-6-pyridyl)methanol (NaTCPM)

The oil obtained from Example 15 was dissolved in 60 ml of toluene. NaOH (50% in water, 2.07 g, 25.9 mmol) diluted with 100 ml of water was added, causing formation of precipitate. The mixture was heated to reflux for an hour with stirring. Solid was dissolved (reacted) to give a homogeneous solution. Upon cooling to room temperature and stopping stirring, the solution phased into two layers. The bottom layer was collected, treated with 0.5 g of activated carbon at 100° C. for 10 minutes, and then filtered. The filtrate was evaporated to yield a white powder, which, after drying in a vacuum oven, weighed 2.88 g, 78% based on TBPM. $^1$H NMR ($D_2O$, δ,TMS): 7.63(t, $J_{H-H}$=4.5 Hz, 3H), 7.80(d, $J_{H-H}$=4.5 Hz, 6H). $^{13}$C NMR ($D_2O$, δ,TMS): 81.8, 122.6, 123.3, 152.4, 161.4, 172.7. LC/APCI/MS: m/e 396 (M−3Na+4H).

Example 17

Synthesis of gadolinium tris(2-carboxy-6-pyridyl)) methanol (GdTCPM)

NaTCPM (1.00 g, 2.2 mmol) (Example 16) was dissolved in 100 ml of deionized water in a reaction flask. Gd(OAc)$_3$.XH$_2$O (34.3% Gd; FW, 458; 0.90 g, 2.0 mmol), dissolved in 50 ml of deionized water was added dropwise with stirring. A white precipitate was obtained at the end of the addition. The volume was reduced to 20 ml and precipitate was filtered, washed with water, and dried to yield 0.92 g, 85% GdTCPM. Karl Fisher Water analysis determined that there were four molecules of water per molecule of GdTCPM. Elemental analysis based on GdTCPM.4H$_2$O (FW: 621.54): Calc. C, 36.71%, H, 2.92%, N, 6.76%, Gd, 25.30; Found: C, 37.71%, H, 2.53%, N, 6.87%, Gd, 26.59. Sodium residue was 0.11%. FAB/MS spectrum fits the computer simulated spectrum for GdTCPM, which had the following structural formula:

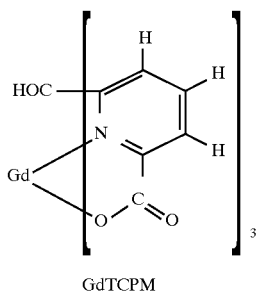

GdTCPM

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound having the formula

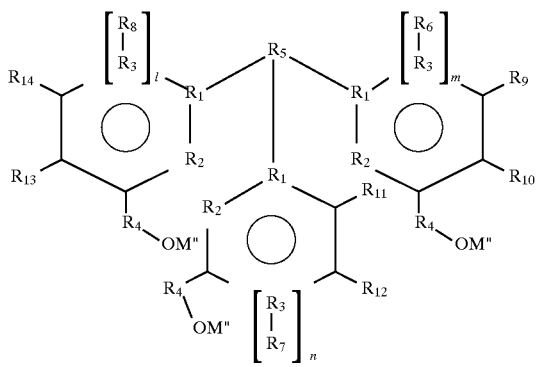

wherein:
l, m and n are independently 0 or 1
$R_1$ is C or N
$R_2$ is N, O or S
$R_3$ is C
$R_4$ is CO, SO$_2$, PO$_2^-$M', or NH,
$R_5$ is selected from the group consisting of
 (a) P
 (b) P=O
 (c) B(R)$^-$M'
 (d) N
 (e) N(CH$_2$)
 (f) N[C(O)]$_3$
 (g) N[CH$_2$C(O)]$_3$
 (h) CH
 (i) COR
 (j) COC(O)N(R)$_2$
 (k) C(CH$_2$OR)(CH$_2$)$_3$
 (l) SiR
wherein R is selected from the group consisting of
 (i) H
 (ii) C$_1$–C$_{20}$ alkyl
 (iii) hydroxyalkyl (C$_1$–C$_{30}$)
 (iv) CH$_2$CH(OH)CH$_2$(O CH$_2$CH(OH)CH$_2$)$_n$OH (n=0–10)
 (v) CH$_2$CH$_2$ (O CH$_2$CH$_2$)$_n$OH (n=0–10)
 (vi) ribose
 (vii) glucose
 (viii) peptide or polypeptide
 (ix) PO$_3^{2-}$2M'
and M' is Na$^+$ or meglumine
$R_6$–$R_{14}$ are each independently selected from the group consisting of
 (a) R
 (b) OR
 (c) N(R)$_2$
 (d) NHC(O)R
 (e) COO$^-$M'
 (f) C(O)N(R)$_2$
 (g) SO$_3^-$M'
wherein R and M' are defined as above, and
M'' is selected from a group consisting of Na, Li, K, NH$_4^\oplus$, and MgBr.

2. The compound as set forth in claim 1 wherein l, m, and n are each 0.

3. The compound as set forth in claim 1 wherein l, m, and n are each 1.

4. The compound as set forth in claim 1 wherein l is 0, and m and n are each 1.

5. The compound as set forth in claim 1 wherein l and m are each 0, and n is 1.

6. The compound having the formula

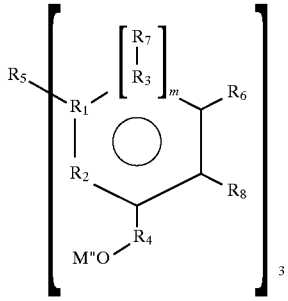

wherein:
m is independently 0 or 1
$R_1$ is C or N
$R_2$ is N, O, or S
$R_3$ is C
$R_4$ is CO, SO$_2$, PO$_2^-$M', or NH,
$R_5$ is selected from the group consisting of
 (a) P
 (b) P=O
 (c) B(R)$^-$M
 (d) N
 (e) N(CH$_2$)
 (f) N[C(O)]$_3$
 (g) N[CH$_2$C(O)]$_3$
 (h) CH
 (i) COR
 (j) COC(O)N(R)$_2$
 (k) C(CH$_2$OR)(CH$_2$)$_3$
 (l) SiR
wherein R is selected from the group consisting of
 (i) H
 (ii) C$_1$–C$_{20}$ alkyl (iii) hydroxylalkyl ($C_1$–$C_{20}$)
(iv) $CH_2CH(OH)CH_2(O\ CH_2CH(OH)CH_2)_nOH$ (n=0–10)
(v) $CH_2CH_2\ (O\ CH_2CH_2)_nOH$ (n=0–10)
(vi) ribose
(vii) glucose
(viii) peptide or polypeptide
(ix) $PO_3^{2-}2M'$
and M' is $Na^+$ or meglumine $R_6$–$R_8$ are each independently selected from the group consisting of
(a) R
(b) OR
(c) $N(R)_2$
(d) NHC(O)R
(e) $COO^-M'$
(f) $C(O)N(R)_2$
(g) $SO_3^-M'$
wherein R and M' are defined as above, and
M" is selected from the group consisting of Na, Li, K, $NH_4^{\oplus}$, and MgBr.

7. The compound as set forth in claim 6 wherein m=0 and $R_1$ and $R_2$ are both N.

8. The compound as set forth in claim 6 wherein m=1 and $R_1$=C and $R_2$=N.

9. The compound as set forth in claim 6 wherein m=0 and $R_1$=C an $R_2$=O.

10. The compound as set forth in claim 6 wherein m=0 and $R_1$=C and $R_2$=S.

11. The compound as set forth in claim 9 wherein $R_4$ is CO.

12. The compound as set forth in claim 8 wherein $R_4$ is CO.

13. A compound having the formula selected from the group consisting of

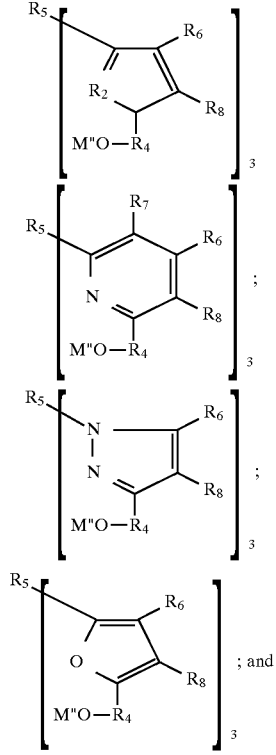

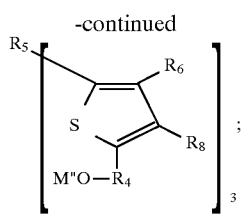

wherein:

$R_2$ is N or S $R_4$ is CO, $SO_2$, $PO_2^-M'$, or NH $R_5$ is selected from the group consisting of
(a) P
(b) P=O
(c) $B(R)^-M'$
(d) N
(e) $N[CH_2)$
(f) $N[C(O)]_3$
(g) $N[CH_2C(O)]_3$
(h) CH
(i) COR
(j) $COC(O)N(R)_2$
(k) $C(CH_2OR)(CH_2)_3$
(l) SiR
wherein R is selected from the group consisting of
(i) H
(ii) $C_1$–$C_{20}$ alkyl
(iii) hydroxyalkyl ($C_1$–$C_{30}$)
(iv) $CH_2CH(OH)CH_2(O\ CH_2CH(OH)CH_2)_nOH$ (n=0–10)
(v) $CH_2CH_2\ (O\ CH_2CH_2)_nOH$ (n=0–10)
(vi) ribose
(vii) glucose
(viii) peptide or polypeptide
(ix) $PO_3^{2-}2M'$
and M' is $Na^+$ or meglumine $R_6$–$R_8$ are each independently selected from the group consisting of
(a) R
(b) OR
(c) $N(R)_2$
(d) NHC(O)R
(e) $COO^-M'$
(f) $C(O)N(R)_2$
(g) $SO_3^-M'$
wherein R and M' are defined as above, and
M" is selected from the group consisting of Na, Li, K, $NH_4^{\oplus}$, and MgBr.

14. The compound as set forth in claim 13 wherein $R_5$ is P=O.

15. The compound as set forth in claim 14 wherein $R_4$ and is CO.

16. The compound as set forth in claim 14 wherein $R_2$ is S and $R_4$ is CO.

17. The compound as set forth in claim 14 wherein M" is Na.

18. A compound having the structural formula

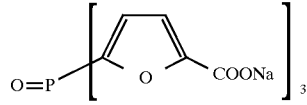

19. A compound having the structural formula

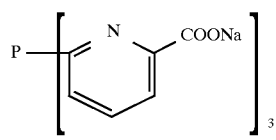

20. A compound having the structural formula

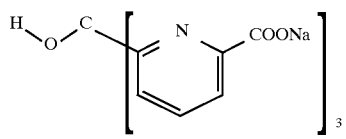

21. A process for preparing tris(6-carboxy-2-pyridyl) phosphine oxide sodium salt which comprises the steps of (a) reacting 2,6-dibromopyridine with n-butyllithium at suitable temperature and pressure conditions to form 2-lithium, 6-bromopyridine;

(b) reacting 2-lithium-6-bromopyridine with phosphous trichloride to form tris(6-bromo-2-pyridyl)phosphine;

(c) reacting said phosphine with sodium cyanide at suitable temperature and pressure conditions to form tris(6-cyano-2-pyridyl)phosphine;

(d) reacting said cyano-phosphine with hydrochloric acid at suitable temperature and pressure conditions to form tris(6-carboxy-2-pyridyl)phosphine hydrochloride; and (e) reacting said phosphine hydrochloride with hydrogen peroxide first and then with sodium bicarbonate to form said tris(6-carboxy-2-pyridyl)phosphine oxide sodium salt, which has the structural formula

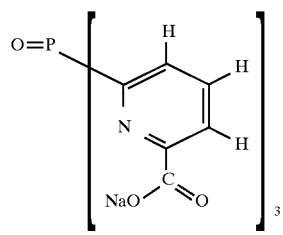

* * * * *